United States Patent [19]
Kambe et al.

[11] Patent Number: 6,099,798
[45] Date of Patent: Aug. 8, 2000

[54] ULTRAVIOLET LIGHT BLOCK AND PHOTOCATALYTIC MATERIALS

[75] Inventors: Nobuyuki Kambe, Menlo Park; Xiangxin Bi, San Ramon, both of Calif.

[73] Assignee: NanoGram Corp., Fremont, Calif.

[21] Appl. No.: 08/962,515

[22] Filed: Oct. 31, 1997

[51] Int. Cl.[7] .................. A61L 2/10; B08B 7/00; B32B 9/00
[52] U.S. Cl. .................. 422/24; 134/1; 428/543; 428/913
[58] Field of Search .................. 422/1, 24, 121, 422/122; 428/546, 570, 34.4, 34.7, 543, 913; 134/1

[56] References Cited

U.S. PATENT DOCUMENTS

| | | |
|---|---|---|
| 3,566,855 | 3/1971 | Morgan . |
| 3,658,539 | 4/1972 | Dantro . |
| 3,709,984 | 1/1973 | Dantro . |
| 3,923,968 | 12/1975 | Basque et al. . |
| 4,241,042 | 12/1980 | Matijevic et al. . |
| 4,548,798 | 10/1985 | Rice . |
| 4,558,017 | 12/1985 | Gupta et al. . |
| 4,574,078 | 3/1986 | Cortesi et al. . |
| 4,687,753 | 8/1987 | Fiato et al. . |
| 4,842,832 | 6/1989 | Inoue et al. . |
| 5,013,706 | 5/1991 | Schramm et al. . |
| 5,035,784 | 7/1991 | Anderson et al. . |
| 5,053,580 | 10/1991 | Schramm et al. . |
| 5,061,473 | 10/1991 | De Cleyn et al. . |
| 5,108,732 | 4/1992 | Krumbe et al. . |
| 5,443,811 | 8/1995 | Karvinen . |
| 5,449,467 | 9/1995 | Taoda et al. . |
| 5,536,448 | 7/1996 | Takahashi et al. . |
| 5,712,461 | 1/1998 | Zhang et al. . |

FOREIGN PATENT DOCUMENTS

| | | |
|---|---|---|
| 704187 | 4/1996 | European Pat. Off. . |
| 9-207263 | 8/1997 | Japan . |
| 9-220477 | 8/1997 | Japan . |

OTHER PUBLICATIONS

Bi et al., J. Mater. Res., vol. 8, No. 7, pp. 1666–1674 (Jul. 1993).
Curcio et al., Applied Surface Science, vol. 46, pp. 225–229 (1990).
Musci et al., J. Mater. Res., vol. 7, No. 10, pp. 2846–2852 (Oct. 1992).
Rice et al., J. Am. Ceram. Soc., vol. 71, No. 4, pp. C–181–C–183 (1988).
Siegel et al., J. Mater. Res., vol. 3, No. 6, pp. 1367–1372 (Nov./Dec. 1988).

*Primary Examiner*—Elizabeth McKane
*Attorney, Agent, or Firm*—Westman, Champlin & Kelly, P.A.; Peter S. Dardi

[57] ABSTRACT

Nanoscale UV absorbing particles are described that have high UV absorption cross sections while being effectively transparent to visible light. These particles can be used to shield individuals from harmful ultraviolet radiation. These particles can also be used in industrial processing especially to produce solid state electronic devices by creating edges of photoresist material with a high aspect ratio. The UV absorbing particles can also be used as photocatalysts that become strong oxidizing agents upon exposure to UV light. Laser pyrolysis provides an efficient method for the production of suitable particles.

19 Claims, 4 Drawing Sheets

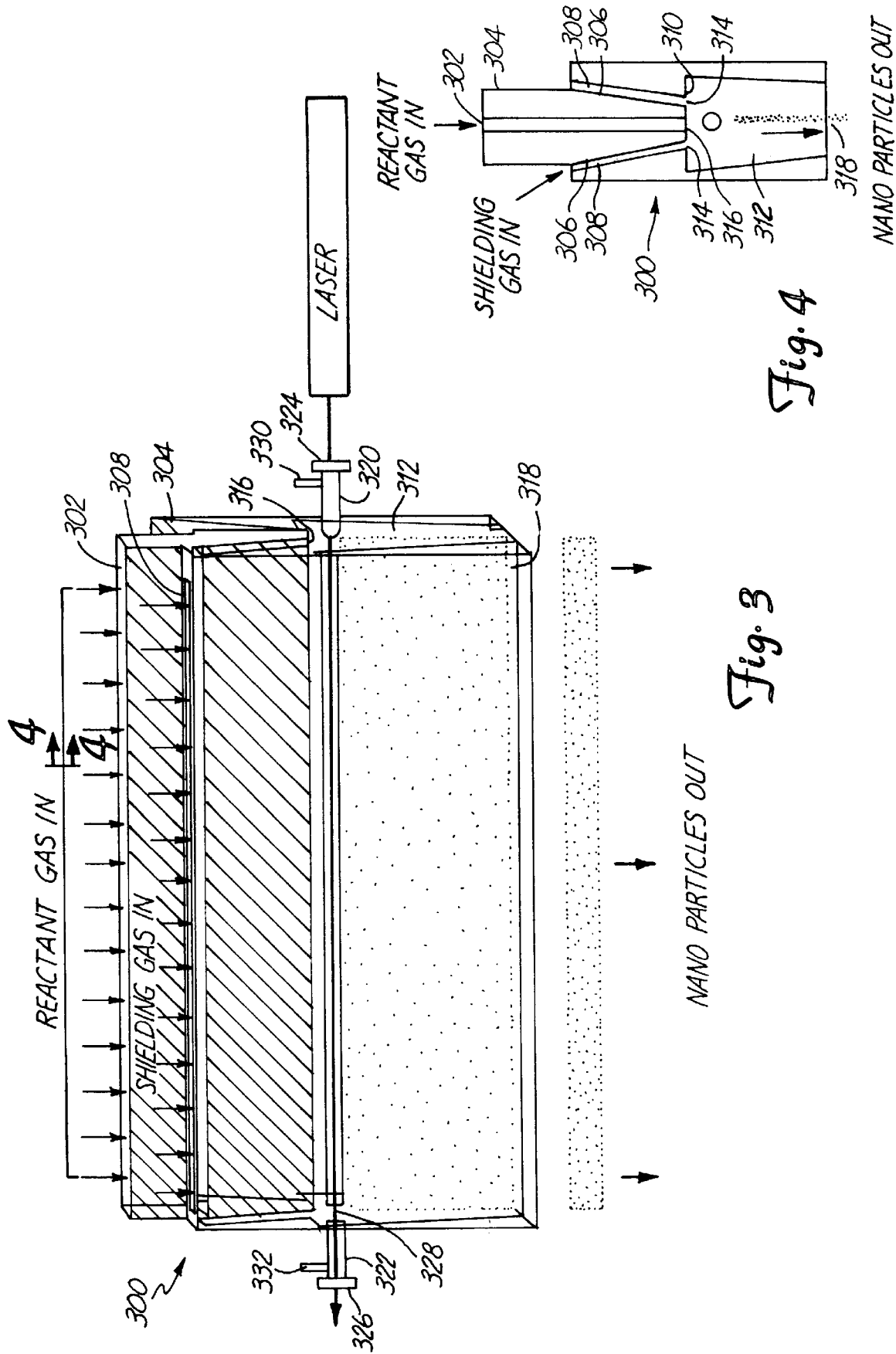

ULTRAVIOLET LIGHT BLOCK AND PHOTOCATALYTIC MATERIALS

FIELD OF THE INVENTION

The present invention relates to metal oxide particles that are effective at absorbing ultraviolet light for use in UV blocks and photocatalytic materials. The invention further relates to methods for the production of the metal oxide particles.

BACKGROUND OF THE INVENTION

While ultraviolet light can be useful in commercial processing, contact with ultraviolet light has a detrimental effect on biological organisms. Harmful ultraviolet light can come from both sun light and from artificial light sources. The risk from exposure to ultraviolet light from natural sun light is increasing in portions of the world due to occasional significant drops in the UV-absorbing ozone layer. Cost effective ways of reducing human exposure to harmful ultraviolet light are desirable.

On the other hand, some commercial processes use UV light as a processing tool. In order to make effective use of UV light in the processing of microscopic components, precise control of the light absorption is advantageous. In addition, photocatalytic materials can catalyze chemical reactions upon exposure to appropriate light. Efficient approaches for utilization of these commercial processes can greatly expand their commercial scope.

SUMMARY OF THE INVENTION

Small particles, especially nanoscale particles, are useful as absorbers of ultraviolet light. Due to their small size, nanoscale particles can be relatively transparent to visible light. Similarly, the UV absorption spectrum-depends on the particle diameters. Laser pyrolysis provides a important source of UV absorbing, nanoscale particles-with relatively narrow distributions of diameters. The particles are useful for producing UV blocking materials. The particles are also very useful for producing sharp boundaries for electrical components on electronic circuit boards produced using photoresist. Also, the UV absorbing particles can be used as photocatalysts that create an oxidizing potential upon illumination with UV light.

In a first aspect, the invention features a light bulb including a light source and a screen substantially transparent to visible light, the screen comprising metal oxide particles having an average diameter less than about 100 nm. The screen can further include a silicon glass or an organic polymer. The light source can include an incandescent filament, a fluorescent light or a halogen light. The particles preferably have an average diameter from about 5 nm to about 50 nm. The metal oxide particles can include titanium dioxide, zinc oxide, zinc dioxide or cerium dioxide.

In another aspect, the invention features a topical ointment including an ointment vehicle and crystalline particles comprising metal oxide, the particles having an average diameter of less than about 100 nm and a diameter distribution such that at least about 95 percent of the particles have a diameter greater than about 60 percent of the average diameter and less than about 140 percent of the average diameter. The crystalline particles preferably have an average diameter from about 5 nm to about 50 nm.

In another aspect, the invention features a window including a substantially transparent substrate and particles comprising metal oxide, the particle having an average diameter of less than about 100 nm. The particles preferably have an average diameter from about 5 nm to about 50 nm.

In another aspect, the invention features a photoresist composition including a photoactivated composition and particles comprising metal oxide, the particles having an average diameter from about 5 nm to about 150 nm.

In another aspect, the invention features a method of producing a UV absorbing layer comprising the step of applying a layer of particles to a substantially transparent substrate at low temperature, the particles comprising metal oxide and having an average particle diameter from about 5 nm to about 100 nm.

In another aspect, the invention features an article comprising a self cleaning surface including discrete particles that are photocatalytic upon exposure to UV light, said particles having an average diameter from about 5 nm to about 150 nm. The self cleaning surface can be mobile. The particles can comprise $TiO_2$. The particles can have a diameter distribution such that at least about 95 percent of the particles have a diameter greater than about 60 percent of the average diameter and less than about 140 percent of the average diameter.

In another aspect, the invention features a method of purifying a fluid comprising the step of contacting the fluid with a surface comprising discrete particles that are photocatalytic upon exposure to UV light, the particles having an average diameter from about 5 nm to about 150 nm, where the surface is exposed to UV light.

In another aspect, the invention features a method of cleaning a hard surface comprising the step of exposing a hard surface to UV light, the hard surface comprising discrete particles that are photocatalytic upon exposure to UV light, said particles having an average diameter from about 5 nm to about 150 nm.

In another aspect, the invention features a method of producing titanium oxide particles comprising the step of pyrolyzing a molecular stream comprising a titanium precursor, an oxidizing agent and a radiation absorbing gas in a reaction chamber, where the pyrolysis is driven by heat absorbed from a laser beam. The laser beam preferably includes infrared light, can be generated by a $CO_2$ laser. The oxidizing agent can be $O_2$, $O_3$, CO or $CO_2$. In a preferred embodiment, the molecular stream is generated by a nozzle substantially elongated in one dimension relative to the orthogonal direction.

Other features and advantages of the invention are evident from the detailed description and claims below.

BRIEF DESCRIPTION OF THE DRAWING

FIG. 3 is a schematic, perspective view of a reaction chamber of an alternative embodiment of the laser pyrolysis apparatus, where the materials of the chamber are depicted as transparent to reveal the interior of the apparatus.

FIG. 4 is a sectional view of the reaction chamber of FIG. 2 taken along line 4—4.

DESCRIPTION OF THE PREFERRED EMBODIMENTS

Metal oxide particles with average diameters less than about 1000 nm and especially less than about 100 nm have been found to be useful components for systems designed to block or to exploit UV light. Titanium dioxide ($TiO_2$) zinc oxide (ZnO), zinc dioxide ($ZnO_2$) and cerium dioxide ($CeO_2$) are of particular interest. Because of the small size of the particles, optical scattering becomes negligible so that the particles become generally transparent to visible light. On the other hand, the UV absorption properties of the particles can be controlled by appropriate selection of the distribution of particle diameters. Laser pyrolysis, as described below, is an efficient method for producing metal oxide particles with a selected average particle diameter and a narrow distribution of diameters.

A basic feature of successful application of laser pyrolysis for the production of nanoscale metal oxide particles is production of a molecular stream containing a metal precursor compound, a radiation absorber and an oxygen source. The molecular stream is pyrolyzed by an intense laser beam. The intense heat resulting from the absorption of the laser radiation induces the oxidation of the metal precursor compound in the oxidizing environment. The laser pyrolysis provides for formation of metal oxides particles that may be difficult to form under thermodynamic equilibrium conditions. As the molecular stream leaves the laser beam, the metal oxide particles are rapidly quenched. The metal oxide particles produced by laser pyrolysis can be subjected to further processing to alter and/or improve the properties of the particles.

Figure 1:
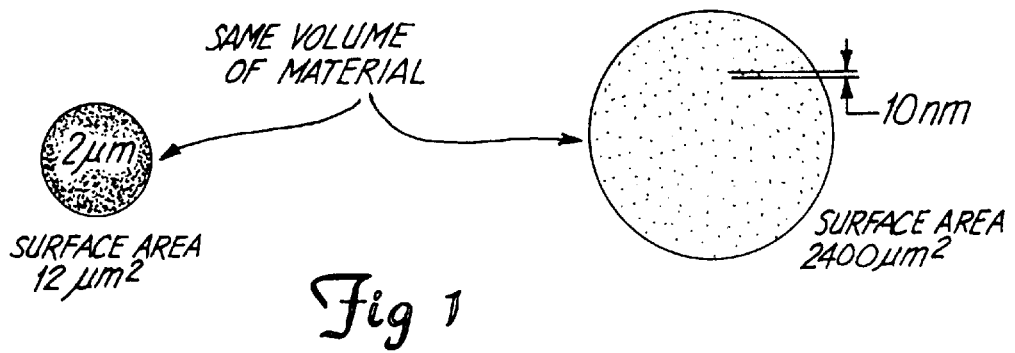
FIG. 1 is a schematic illustration of the effect on surface area due to a reduction in particle diameter.

The small size of the particles results in a significantly increased surface area for a given weight of material. The increased surface area is depicted graphically in FIG. 1., assuming spherical particles and no aggregation. The increased surface area of the particles can be directly advantageous for certain applications such as catalysis. In addition, a large surface area may enhance the UV absorption cross section for a given quantity of material.

A. Particle Production

Laser pyrolysis has been discovered to be a valuable tool for the production of nanoscale metal oxide particles of interest. In addition, the metal oxide particles produced by laser pyrolysis are a convenient material for further processing to expand the pathways for the production of desirable metal oxide particles. Thus, using laser pyrolysis alone or in combination with additional processes, a wide variety of metal oxide particles can be produced. In some cases, alternative production pathways can be followed to produce comparable particles.

The reaction conditions determine the qualities of the metal oxide particles produced by laser pyrolysis. The reaction conditions for laser pyrolysis can be controlled relatively precisely in order to produce particles with desired properties. The appropriate reaction conditions to produce a certain type of particles generally depend on the design of the particular apparatus. Nevertheless, some general observations can be made on the relationship between reaction conditions and the resulting particles.

Increasing the laser power results in increased reaction temperatures in the reaction region as well as a faster quenching rate. A rapid quenching rate tends to favor production of higher energy structures. Similarly, increasing the chamber pressure also tends to favor the production of higher energy structures. Also, increasing the concentration of oxygen source in the reactant stream favors the production of metal oxides with increased amounts of oxygen, i.e., higher oxidation states of the metal, for metals that multiple, stable oxidation states.

Reactant gas flow rate and velocity of the reactant gas stream are inversely related to particle size so that increasing the reactant gas flow rate or velocity tends to result in smaller particle size. Also, the growth dynamics of the particles have a significant influence on the size of the resulting particles. In other words, different crystal forms of metal oxide have a tendency to form different size particles from other crystal forms under relatively similar conditions. Laser power also influences particle size with increased laser power favoring larger particle formation for lower melting materials and smaller particle formation for higher melting materials.

Appropriate precursor compounds generally include metal compounds with reasonable vapor pressures, i.e., vapor pressures sufficient to get desired amounts of precursor vapor in the reactant stream. The vessel holding the precursor compounds can be heated to increase the vapor pressure of the metal compound precursor, if desired. Preferred titanium precursors include, for example, $TiCl_4$, $Ti(CH_3)_4$ and $Ti[OCH(CH_3)_2]_4$ (titanium tetra-I-propoxide). Preferred cerium precursors include, for example, $Ce(OC_3H_7)_4$ (cerium i-propoxide), and $(C_5H_5)_3Ce$ (tris (cyclopentadienyl)cerium). Preferred zinc precursors include, for example, $ZnCl_2$. $ZnCl_2$ vapor can be generated by heating and, optionally, melting $ZnCl_2$ solids. For example, $ZnCl_2$ has a vapor pressure of about 5 mm Hg at a temperature of about 500° C. When using $ZnCl_2$ precursor, the chamber and nozzle preferably are heated to avoid getting condensation of the precursor.

Preferred oxygen sources include, for example, $O_2$, CO, $CO_2$, $O_3$ and mixtures thereof. The oxygen source should not react significantly with the metal precursor compound prior to entering the reaction zone since this generally would result in the formation of large particles.

Laser pyrolysis can be performed with a variety of optical laser frequencies. Preferred lasers operate in the infrared portion of the electromagnetic spectrum. $CO_2$ lasers are particularly preferred sources of laser light. Infrared absorbers for inclusion in the molecular stream include, for example, $C_2H_4$, $NH_3$, $SF_6$ and $O_3$. $O_3$ can act as both an infrared absorber and as an oxygen source. The radiation absorber, such as the infrared absorber, absorbs energy from the radiation beam and distributes the energy as heat to the other reactants to drive the pyrolysis.

Preferably, the energy absorbed from the radiation beam increases the temperature at a tremendous rate, many times the rate that energy generally would be produced even by strongly exothermic reactions under controlled condition. While the process generally involves nonequilibrium conditions, the temperature can be described approximately based on the energy in the absorbing region. The laser pyrolysis process is qualitatively different from the process in a combustion reactor where an energy source initiates a reaction, but the reaction is driven by energy given off by an exothermic reaction.

An inert shielding gas can be used to reduce the amount of reactant and product molecules contacting the reactant chamber components. For the production of titanium dioxide, zinc oxides and cerium dioxide particles, appropriate shielding gases include, for example, Ar, He and $N_2$.

An appropriate laser pyrolysis apparatus generally includes a reaction chamber isolated from the ambient environment. A reactant inlet connected to a reactant supply system produces a molecular stream through the reaction chamber. A laser beam path intersects the molecular stream at a reaction zone. The molecular stream continues after the reaction zone to an outlet, where the molecular stream exits the reaction chamber and passes into a collection system. Generally, the laser is located external to the reaction chamber, and the laser beam enters the reaction chamber through an appropriate window.

Figure 2:
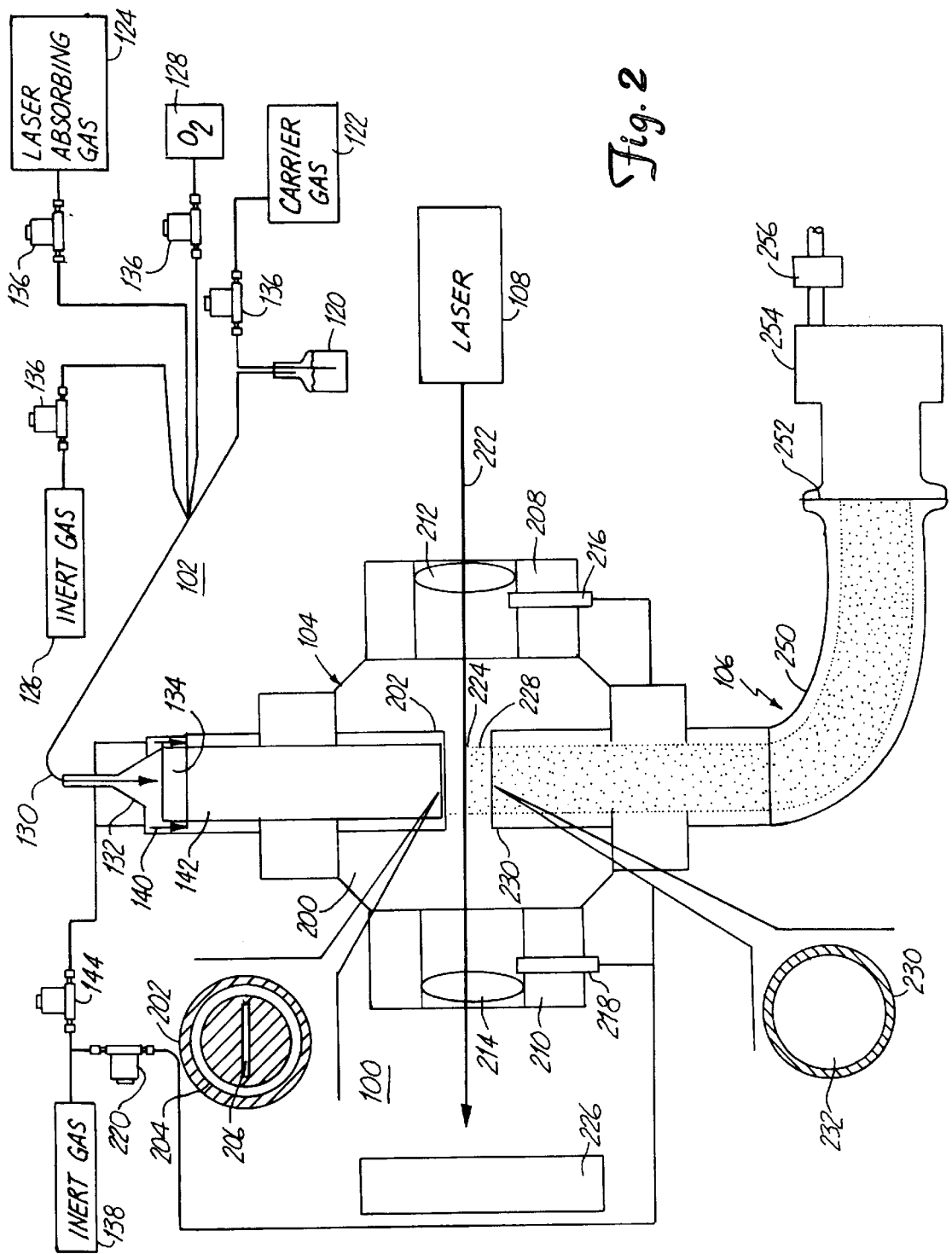
FIG. 2 is a schematic, sectional view of an embodiment of a laser pyrolysis apparatus taken through the middle of the laser radiation path. The upper insert is a bottom view of the injection nozzle, and the lower insert is a top view of the collection nozzle.

Referring to FIG. 2, a particular embodiment 100 of a pyrolysis apparatus involves a reactant supply system 102, reaction chamber 104, collection system 106 and laser 108. Reactant supply system 102 includes a source 120 of metal precursor compound. For liquid precursors, a carrier gas from carrier gas source 122 can be introduced into precursor source 120, containing liquid precursor to facilitate delivery of the precursor. The carrier gas from source 122 preferably is either an infrared absorber or an inert gas and is preferably bubbled through the liquid, metal precursor compound. The quantity of precursor vapor in the reaction zone is roughly proportional to the flow rate of the carrier gas.

Alternatively, carrier gas can be supplied directly from infrared absorber source 124 or inert gas source 126, as appropriate. The oxidizing agent is supplied from source 128, which can be a gas cylinder or other appropriate container. The gases from the metal precursor compound source 120 are mixed with gases from oxidizing agent source 128, infrared absorber source 124 and inert gas source 126 by combining the gases in a single portion of tubing 130. The gases are combined a sufficient distance from reaction chamber 104 such that the gases become well mixed prior to their entrance into reaction chamber 104. The combined gas in tube 130 passes through a duct 132 into rectangular channel 134, which forms part of an injection nozzle for directing reactants into the reaction chamber.

Flow from sources 122, 124, 126 and 128 are preferably independently controlled by mass flow controllers 136. Mass flow controllers 136 preferably provide a controlled flow rate from each respective source. Suitable mass flow controllers include, for example, Edwards Mass Flow Controller, Model 825 series, from Edwards High Vacuum International, Wilmington, Mass.

Inert gas source 138 is connected to an inert gas duct 140, which flows into annular channel 142. A mass flow controller 144 regulates the flow of inert gas into inert gas duct 140. Inert gas source 126 can also function as the inert gas source for duct 140, if desired.

The reaction chamber 104 includes a main chamber 200. Reactant supply system 102 connects to the main chamber 200 at injection nozzle 202. The end of injection nozzle 202 has an annular opening 204 for the passage of inert shielding gas, and a rectangular slit 206 for the passage of reactant gases to form a molecular stream in the reaction chamber. Annular opening 204 has, for example, a diameter of about 1.5 inches and a width along the radial direction of about 1/16 in. The flow of shielding gas through annular opening 204 helps to prevent the spread of the reactant gases and product particles throughout reaction chamber 104.

Tubular sections 208, 210 are located on either side of injection nozzle 202. Tubular sections 208, 210 include ZnSe windows 212, 214, respectively. Windows 212, 214 are about 1 inch in diameter. Windows 212, 214 are preferably plane-focusing lenses with a focal length equal to the distance between the center of the chamber to the surface of the lens to focus the beam to a point just below the center of the nozzle opening. Windows 212, 214 preferably have an antireflective coating. Appropriate ZnSe lenses are available from Janos Technology, Townshend, Vt. Tubular sections 208, 210 provide for the displacement of windows 212, 214 away from main chamber 200 such that windows 212, 214 are less likely to be contaminated by reactants or products. Window 212, 214 are displaced, for example, about 3 cm from the edge of the main chamber 200.

Windows 212, 214 are sealed with a rubber o-ring to tubular sections 208, 210 to prevent the flow of ambient air into reaction chamber 104. Tubular inlets 216, 218 provide for the flow of shielding gas into tubular sections 208, 210 to reduce the contamination of windows 212, 214. Tubular inlets 216, 218 are connected to inert gas source 138 or to a separate inert gas source. In either case, flow to inlets 216, 218 preferably is controlled by a mass flow controller 220.

Laser 108 is aligned to generate a laser beam 222 that enters window 212 and exits window 214. Windows 212, 214 define a laser light path through main chamber 200 intersecting the flow of reactants at reaction zone 224. After exiting window 214, laser beam 222 strikes power meter 226, which also acts as a beam dump. An appropriate power meter is available from Coherent Inc., Santa Clara, Calif. Laser 108 can be replaced with an intense conventional light source such as an arc lamp. Preferably, laser 108 is an infrared laser, especially a CW $CO_2$ laser such as an 1800 watt maximum power output laser available from PRC Corp., Landing, N.J.

Reactants passing through slit 206 in injection nozzle 202 initiate a molecular stream. The molecular stream passes through reaction zone 224, where reaction involving the metal precursor compound takes place. Heating of the gases in reaction zone 224 is extremely rapid, roughly on the order of $10^5 °C./sec$ depending on the specific conditions. The reaction is rapidly quenched upon leaving reaction zone 224, and nanoparticles 228 are formed in the molecular stream. The nonequilibrium nature of the process allows for the production of nanoparticles with a highly uniform size distribution and structural homogeneity.

The path of the molecular stream continues to collection nozzle 230. Collection nozzle 230 is spaced about 2 cm from injection nozzle 202. The small spacing between injection nozzle 202 and collection nozzle 230 helps reduce the contamination of reaction chamber 104 with reactants and products. Collection nozzle 230 has a circular opening 232. Circular opening 232 feeds into collection system 106.

The chamber pressure is monitored with a pressure gauge attached to the main chamber. The chamber pressure generally ranges from about 5 Torr to about 1000 Torr. The preferred chamber pressure for the production of titanium oxides, zinc oxides and cerium oxides ranges from about 40 Torr to about 400 Torr.

Reaction chamber 104 has two additional tubular sections not shown. One of the additional tubular sections projects into the plane of the sectional view in FIG. 2, and the second additional tubular section projects out of the plane of the sectional view in FIG. 2. When viewed from above, the four tubular sections are distributed roughly, v symmetrically around the center of the chamber. These additional tubular sections have windows for observing the inside of the chamber. In this configuration of the apparatus, the two additional tubular sections are not used to facilitate production of nanoparticles.

Collection system 106 can include a curved channel 250 leading from collection nozzle 230. Because of the buoyant nature of the nanoparticles, the product nanoparticles follow the flow of the gas around curves. Collection system 106 includes a filter 252 within the gas flow to collect the product nanoparticles. A variety of materials such as teflon, glass fibers and the like can be used for the filter as long as the material is inert and has a fine enough mesh to trap the particles. Preferred materials for the filter include, for example, a glass fiber filter from ACE Glass Inc., Vineland, N.J.

Pump 254 is used to maintain collection system 106 at a reduced pressure. A variety of different pumps can be used. Appropriate pumps 254 include, for example, Busch Model B0024 pump from Busch, Inc., Virginia Beach, Va. with a pumping capacity of about 25 cubic feet per minute (cfm) and Leybold Model SV300 pump from Leybold Vacuum Products, Export, Pa. with a pumping capacity of about 195 cfm. It may be desirable to flow the exhaust of the pump through a scrubber 256 to remove any remaining reactive chemicals before venting into the atmosphere. The entire apparatus 100 can be placed in a fume hood for ventilation purposes and for safety considerations. Generally, the laser remains outside of the fume hood because of its large size.

The apparatus is controlled by a computer. Generally, the computer controls the laser and monitors the pressure in the reaction chamber. The computer can be used to control the flow of reactants and/or the shielding gas. The pumping rate is controlled by either a manual needle valve or an automatic throttle valve inserted between pump 254 and filter 252. As the chamber pressure increases due to the accumulation of particles on filter 252, the manual valve or the throttle valve can be adjusted to maintain the pumping rate and the corresponding chamber pressure.

The reaction can be continued until sufficient nanoparticles are collected on filter 252 such that the pump can no longer maintain the desired pressure in the reaction chamber 104 against the resistance through filter 252. When the pressure in reaction chamber 104 can no longer be maintained at the desired value, the reaction is stopped, and the filter 252 is removed. With this embodiment, about 3–75 grams of nanoparticles can be collected in a single run before the chamber pressure can no longer be maintained. A single run generally can last from about 10 minutes to about 3 hours depending on the type of particle being produced and the particular filter. Therefore, it is straightforward to produce a macroscopic quantity of nanoparticles, i.e., a quantity visible with the naked eye.

The reaction conditions can be controlled relatively precisely. The mass flow controllers are quite accurate. The laser generally has about 0.5 percent power stability. With either a manual control or a throttle valve, the chamber pressure can be controlled to within about 1 percent.

The configuration of the reactant supply system 102 and the collection system 106 can be reversed. In this alternative configuration, the reactants are supplied from the bottom of the reaction chamber, and the product particles are collected from the top of the chamber. This alternative configuration tends to result in a slightly higher collection of product since metal oxide nanoscale particles generally are buoyant in the surrounding gases. In this configuration, it is preferable to include a curved section in the collection system so that the collection filter is not mounted directly above the reaction chamber.

An alternative design of a laser pyrolysis apparatus has been described. See, commonly assigned, copending U.S. patent application Ser. No. 08/808,850, entitled "Efficient Production of Particles by Chemical Reaction," incorporated herein by reference. This alternative design is intended to facilitate production of commercial quantities of nanoparticles. A variety of configurations are described for injecting the reactant materials into the reaction chamber.

The alternative apparatus includes a reaction chamber designed to minimize contamination of the walls of the chamber with particles, to increase the production capacity and to make efficient use of resources. To accomplish these objectives, the reaction chamber conforms generally to the shape of an elongated reactant inlet, decreasing the dead volume outside of the molecular stream. Gases can accumulate in the dead volume, increasing the amount of wasted radiation through scattering or absorption by nonreacting molecules. Also, due to reduced gas flow in the dead volume, particles can accumulate in the dead volume causing chamber contamination.

The design of the improved reaction chamber 300 is schematically shown in FIGS. 3 and 4. A reactant gas channel 302 is located within block 304. Facets 306 of block 304 form a portion of conduits 308. Another portion of conduits 308 join at edge 310 with an inner surface of main chamber 312. Conduits 308 terminate at shielding gas inlets 314. Block 304 can be repositioned or replaced, depending on the reaction and desired conditions, to vary the relationship between the elongated reactant inlet 316 and shielding gas inlets 314. The shielding gases from shielding gas inlets 314 form blankets around the molecular stream originating from reactant inlet 316.

The dimensions of elongated reactant inlet 316 preferably are designed for high efficiency particle production. Reasonable dimensions for the reactant inlet for the production of metal oxide particle, when used with a 1800 watt $CO_2$ laser, are from about 5 mm to about 1 meter.

Main chamber 312 conforms generally to the shape of elongated reactant inlet 316. Main chamber 312 includes an outlet 318 along the molecular stream for removal of particulate products, any unreacted gases and inert gases. Tubular sections 320, 322 extend from the main chamber 312. Tubular sections 320, 322 hold windows 324, 326 to define a laser beam path 328 through the reaction chamber 300. Tubular sections 320, 322 can include shielding gas inlets 330, 332 for the introduction of shielding gas into tubular sections 320, 322.

The improved apparatus includes a collection system to remove the nanoparticles from the molecular stream. The collection system can be designed to collect a large quantity of particles without terminating production or, preferably, to run in continuous production by switching between different particle collectors within the collection system. The collection system can include curved components within the flow path similar to curved portion of the collection system shown in FIG. 2. The configuration of the reactant injection components and the collection system can be reversed such that the particles are collected at the top of the apparatus.

As noted above, properties of the metal oxide nanoparticles can be modified by further processing. For example, the heating process can be used to increase the uniformity and/or crystallinity of the particles and possibly to remove adsorbed compounds on the particles. In addition, the metal oxide particles can be heated in an oven to alter the oxygen content and/or crystal structure of the metal oxide. The atmosphere surrounding the particles in the oven can be an oxidizing environment or an inert environment. It has been discovered that use of mild conditions, i.e., temperatures well below the melting point of the nanoparticles, can result in modification of the stoichiometry or crystal structure of metal oxides without significantly sintering the nanoparticles into larger particles. This processing in an oven is further discussed in commonly assigned, copending U.S. patent application Ser. No. 08/897,903, entitled "Processing of Vanadium Oxide Particles With Heat," incorporated herein by reference.

Figure 5:
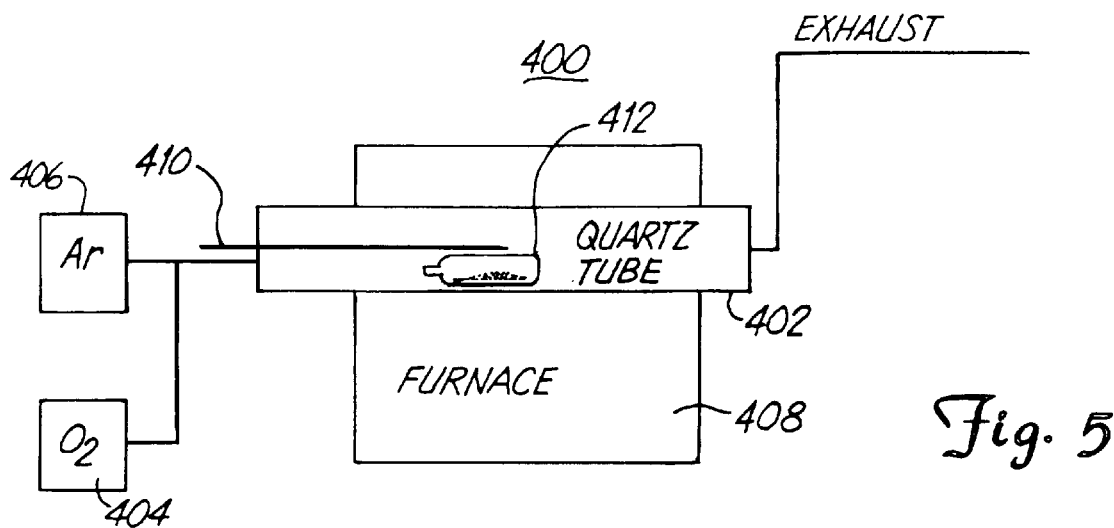
FIG. 5 is a schematic, sectional view of an oven for heating particles, in which the section is taken through the center of the quartz tube.

An example of an apparatus 400 to perform this heat processing is displayed in FIG. 5. Apparatus 400 includes a tube 402 into which the nanoparticles are placed. Tube 402 is connected to an oxidizing gas source 404 and inert gas source 406. Oxidizing gas, inert gas or a combination thereof to produce the desired atmosphere are placed within tube 402.

Preferably, the desired gases are flowed through tube 402. Appropriate active gases to produce an oxidizing environment (oxidizing gas) include, for example, $O_2$, $O_3$, CO, $CO_2$ and combinations thereof. The oxidizing gases can be diluted with inert gases such as Ar, He and $N_2$. The gases in tube 402 can be exclusively inert gases, if desired.

Tube 402 is located within oven or furnace 408. Oven 408 maintains the relevant portions of the tube at a relatively constant temperature, although the temperature can be varied systematically through the processing step, if desired. Temperature in oven 408 generally is measured with a thermocouple 410. The metal oxide particles can be placed in tube 402 within a vial 412. Vial 412 prevents loss of the particles due to gas flow. Vial 412 generally is oriented with the open end directed toward the direction of the source of the gas flow.

The precise conditions including type of oxidizing gas (if any), concentration of oxidizing gas, pressure or flow rate of gas, temperature and processing time can be selected to produce the desired type of product material. The temperatures generally are mild, i.e., significantly below the melting point of the material. The use of mild conditions avoids interparticle sintering resulting in larger particle sizes. Some controlled sintering of the metal oxide particles can be performed in oven 408 at somewhat higher temperatures to produce slightly larger average particle diameters.

For the processing of titanium dioxide or zinc oxide, the temperatures preferably range from about 50° C. to about 1000° C., more preferably from about 50° C. to about 500° C., and even more preferably from about 50° C. to about 200° C. The nanoparticles preferably are heated for about 1 hour to about 100 hours. Some empirical adjustment may be required to produce the conditions appropriate for yielding a desired material.

B. Particle Properties

A collection of preferred metal oxide particles, such as titanium dioxide, zinc dioxide or cerium dioxide particles, has an average diameter of less than a micron, preferably from about 5 nm to about 500 nm and more preferably from about 5 nm to about 100 nm, and even more preferably from about 5 nm to about 50 nm. The particles generally have a roughly spherical gross appearance. Upon closer examination, the particles generally have facets corresponding to the underlying crystal lattice. Nevertheless, the particles tend to exhibit growth that is roughly equal in the three physical dimensions to give a gross spherical appearance. Diameter measurements on particles with asymmetries are based on an average of length measurements along the principle axes of the particle. The measurements along the principle axes preferably are each less than about 1 micron for at least about 95 percent of the nanoparticles, and more preferably for at least about 98 percent of the nanoparticles.

Because of their small size, the particles tend to form loose agglomerates due to van der Waals forces between nearby particles. Nevertheless, the nanometer scale of the particles is clearly observable in transmission electron micrographs of the particles. For crystalline particles, the particle size generally corresponds to the crystal size. The particles generally have a surface area corresponding to particles on a nanometer scale as observed in the micrographs. Furthermore, the particles manifest unique properties due to their small size and large surface area per weight of material.

One manifestation of the small size of the particles is their transparency with respect to visible light for particles that have a diameter smaller than about 50 nm. Particles with a diameter smaller than about 50 nm are transparent because they do not significantly scatter or absorb visible light. These particles also exhibit a modified UV absorption spectrum that reflects the distribution of particle diameters.

As produced, the particles preferably have a high degree of uniformity in size. As determined from examination of transmission electron micrographs, the particles generally have a distribution in sizes such that at least about 95 percent of the particles have a diameter greater than about 40 percent of the average diameter and less than about 160 percent of the average diameter. Preferably, the nanoparticles have a distribution of diameters such that at least about 95 percent of the particles have a diameter greater than about 60 percent of the average diameter and less than about 140 percent of the average diameter. The narrow size distributions can be exploited in a variety of applications, as described below. For some of the applications, it may be desirable to mix particles having narrow diameter distributions to produce a desired distribution of particle diameters.

In addition, the nanoparticles generally have a very high purity level. Metal oxide nanoparticles produced by the above methods are expected to have a purity greater than the reactant gases because the crystal formation process tends to exclude contaminants from the lattice. Furthermore, metal oxide particles produced by laser pyrolysis have been found to have a high degree of crystallinity.

Titanium dioxide is known to exist in three crystalline phases, anatase, rutile and brookite, as well as an amorphous phase. The anatase and rutile phases have a tetrahedral crystal lattice, and the brookite phase has an orthorhombic crystal structure. Although under certain conditions mixed phase material can be formed, laser pyrolysis generally can be effectively used to produce single phase crystalline particles. The conditions of the laser pyrolysis can be varied to favor the formation of a single, selected phase of $TiO_2$. In addition, heating of small metal oxide particles under mild conditions can be used to effectively alter the phase or composition of the materials.

Zinc oxides can have a stoichiometry of, at least, ZnO (hexagonal, Wurtzite structure) or $ZnO_2$. Cerium oxides are known with stoichiometries of $CeO_2$ (cubic, fluorite structure) and $Ce_2O_3$ (hexagonal, Lanthanum oxide structure) as well as nonstiochiometric variations on these materials. Production parameters can be varied to select for a particular stoichiometry of zinc oxide and cerium oxide.

C. UV Block Compositions

Figure 6:
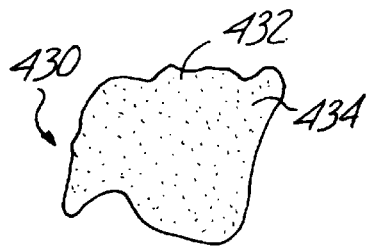
FIG. 6 is a schematic representation of an ointment of the invention.

UV block compositions are useful for a variety of applications. For example, UV block compositions are useful in ointments for application to prevent personal exposure, as materials to prevent passage of UV light from a source into a protected environment and in processing for controlling the path of UV light. Referring to FIG. 6, topical ointments 430 generally involve an ointment vehicle 432 and UV absorbing particles 434. The ointment vehicle can be aqueous based, oil based or solid based. A variety of ointment vehicles are known in the art, for example, as described in U.S. Pat. No. 4,842,832, incorporated herein by reference. The topical ointment can take the form of a sun screen, a cosmetic, and the like. The UV particles can be selected to block out a desired portion of the UV spectrum, as described further below.

Blocking out UV light from a protected environment can involve blocking UV light from a natural (i.e., solar) light source or from artificial light sources. Blocking UV light from natural light generally involves production of a window that selectively is transparent for visible light while absorbing UV light. Windows are any surfaces through which light is transmitted, regardless of shape or location. The $TiO_2$, ZnO, $ZnO_2$ and $CeO_2$ particles described above are particularly suitable for this application because of their relative transparency with respect to visible light.

Figure 7:
FIG. 7 is a schematic representation of UV block materials incorporated into a substrate.

The window can be made from an inorganic glass such as a silicon based glass, an organic polymer such as high density polyethylene and polyesters, and the like. The particles can be placed as a coating on the window or the particles can be dispersed within the window material (FIG. 7). A coating can be applied in a variety of ways such as spray coating of a solvent dispersion, spin coating and deposition of a particle stream.

Figure 8:
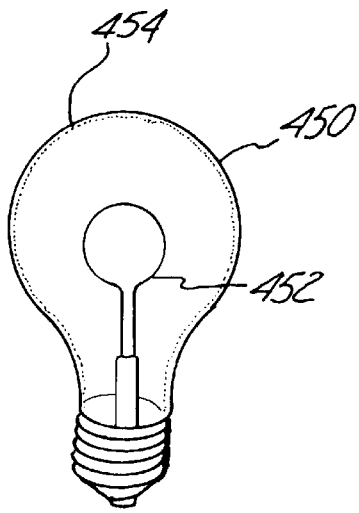
FIG. 8 is a schematic representation of the incorporation of the UV block particles into a light source.

With respect to artificial light sources, the lights generally have a substantially transparent enclosure. The particles described herein can be incorporated into the enclosure to absorb the UV light without substantially reducing the amount of visible light from the light source, as depicted in FIG. 8. As shown in FIG. 8, the enclosure 450 around light source 452 includes a coating 454 of nanoparticles. The light source can be an incandescent light, a fluorescent light, a halogen light, or the any similar light source.

Photoresist compositions are used in the production of solid state electronic devices. A particularly important application of UV block materials in processing involves the incorporation of the materials into photoresist materials to sharpen transmission edges. The objective is to achieve a high aspect ratio of a pattern made by UV-light lithography. The production of ever smaller structures corresponding to electronic components on a substrate requires careful demarcation at the edge of photoresist material used to produce the structures. The current technology uses both conventional UV light sources and excimer lasers as the UV light source.

Figure 9:
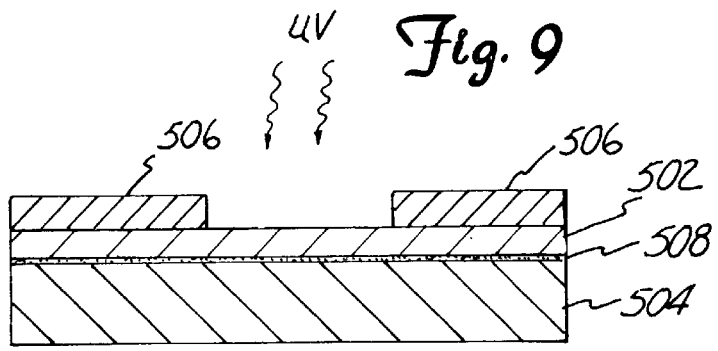
FIG. 9 is a schematic representation of UV absorbing particles used in combination with photoresist to obtain higher-definition edges in patterns on a substrate.

Referring to FIG. 9, the photoresist material 502 is generally applied over a surface 504 of a substrate at specific locations to be patterned. The patterning is performed by irradiating the surface with UV light through a mask 506 such that selected portions of the photoresist 502 are illuminated. The photoresist material 502 is sensitive to UV light so that it can be processed after exposure to UV light. The surface of the substrate 504 can reflect incident and transmitted light to further blur edges 506 resulting in a low aspect ratio of the pattern.

Figure 10:
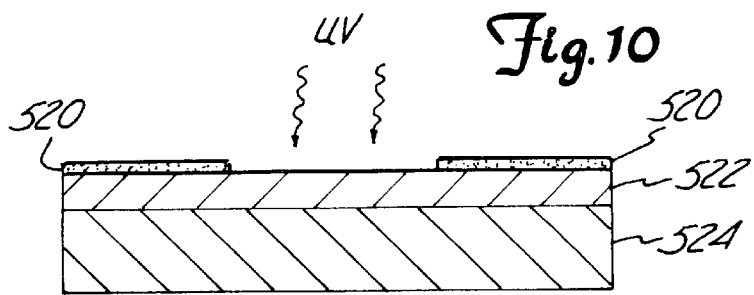
FIG. 10 is a schematic representation of the use of UV absorbing particles as a mask to pattern photoresist on a substrate.

The use of UV absorbing material in the photoresist can reduce these effects. The UV absorbing particles 508 can be applied to the substrate 504, as shown in FIG. 9. The particles can be applied directly to the substrate or as a composition including particles embedded in a polymer matrix. The particle absorb UV light to inhibit the reflection of the light from the surface of the substrate. The preferred UV absorbing particles described herein can be used effectively to absorb UV light with small quantities of material to yield very small patterns on the substrate as a result of a high aspect ratio. Furthermore, the small size of the particles further provides for the production of physically sharp edges for the photoresist material. In another embodiment, the UV absorbing particles 520 are patterned on a layer of photoresist 522 to form a mask, as shown in FIG. 10. The photoresist is layered onto a substrate 524 to be patterned. Alternatively, the UV absorbing particles can be mixed with the photoresist material.

Crystalline particles of $TiO_2$, ZnO, $ZnO_2$ and $CeO_2$ with average diameters less than about 100 nm have particularly suitable properties for the production of UV block materials. These materials are substantially transparent to visible light. Due to quantum effects in particles with diameters below about 100 nm and especially below about 50 nm, the energy band gap widens and the UV absorption spectrum become sharper with an enhanced absorption capability.

To design appropriate block for a particular light source, the UV spectrum of the source is first determined. One can then select the UV absorbing particles to adequately absorb the UV light from the source. For use in absorbing UV light from natural sun light or UV components of light from an artificial light source, preferably a coating of UV absorbing particles preferably absorbs greater than about 75 percent and more preferably greater than about 90 percent of the UV light. It may be desirable to preferentially absorb UV B light, which can be more harmful to humans.

D. Photocatalytic Activity

Under UV light, certain UV absorbing particles such as $TiO_2$ and ZnO become strong oxidizing agents. This oxidizing capability can be exploited by using the particles as photocatalysts. These properties are especially useful for environmentally benign purification and clean-up.

Using particles with a small average diameter and a narrow diameter distribution, the absorption efficiency of the particles generally is localized over a narrow frequency range. Then, the photocatalytic process can be made more efficient by using a UV source with an emission spectrum designed for efficient absorption by the particular metal oxide particles. Furthermore, the use of appropriately small diameter particles results in particles that are transparent to visible light.

Generally, the selected particles are placed in the surface of a substrate. The substrate can be any suitable material. Generally, the substrate is selected such that the photocatalyst particles do not react with the substrate. If the substrate is transparent to visible light, the substrate with the addition of suitably small particles also is transparent. The substrate surface then is contacted with the material to be cleaned. For example, water containing dirt, oil and the like can be placed within a vessel with a coating of the particles. Upon exposure to UV light, the water is cleaned by the strong oxidizing power of the particles. If the substrate is transparent to UV light, the UV light can be projected toward the particles from either direction. Air purification can be accomplished in a similar fashion.

Hard surface cleaning can be accomplished by adapting this approach. The surface to be cleaned can be appropriately coated with suitable metal oxide particles. The surface can be stationary such as a floor or mobile such as a cutting board surface or a plate. The surface is used until it is ready to be cleaned. Then, the surface is exposed to UV light to induce photocatalytic activity. If the surface is mobile, the coated object can be placed in a cleaning apparatus for exposure to UV light.

The embodiments described above are intended to be representative and not limiting. Additional embodiments of the invention are within the claims. As will be understood by those skilled in the art, many changes in the methods and apparatus described above may be made by the skilled practitioner without departing from the spirit and scope of the invention, which should be limited only as set forward in the claims which follow.

What is claimed is:

1. An article comprising a self cleaning surface comprising discrete particles that are photocatalytic upon exposure to UV light, the particles having an average diameter from about 5 nm to about 100 nm.

2. The article of claim 1 wherein the self cleaning surface is mobile.

3. The article of claim 1 wherein the particles comprise $TiO_2$.

4. The article of claim 1 wherein the particles have a diameter distribution such that at least about 95 percent of the particles have a diameter greater than about 60 percent of the average diameter and less than about 140 percent of the average diameter.

5. The article of claim 1 wherein the particles have an average diameter from about 5 nm to about 50 nm.

6. The article of claim 1 wherein the particles have a diameter distribution such that at least about 95 percent of the particles have a diameter greater than about 40 percent of the average diameter and less than about 160 percent of the average diameter.

7. The method of claim 1 wherein the particles comprise ZnO.

8. A method of purifying a fluid comprising contacting the fluid with a surface comprising discrete particles that are photocatalytic upon exposure to UV light, the particles having an average diameter from about 5 nm to about 100 nm, where the surface is exposed to UV light.

9. The method of claim 8 wherein the particles have an average diameter from about 5 nm to about 50 nm.

10. The method of claim 8 wherein the particles comprise $TiO_2$.

11. The method of claim 8 wherein the particles comprise ZnO.

12. The method of claim 8 wherein the particles have a diameter distribution such that at least about 95 percent of the particles have a diameter greater than about 40 percent of the average diameter and less than about 160 percent of the average diameter.

13. The method of claim 8 wherein the particles have a diameter distribution such that at least about 95 percent of the particles have a diameter greater than about 60 percent of the average diameter and less than about 140 percent of the average diameter.

14. A method of cleaning a hard surface comprising exposing a hard surface to UV light, the hard surface comprising discrete particles that are photocatalytic upon exposure to UV light, the particles having an average diameter from about 5 nm to about 100 nm.

15. The method of claim 14 wherein the particles have an average diameter from about 5 nm to about 50 nm.

16. The method of claim 14 wherein the particles comprise $TiO_2$.

17. The method of claim 14 wherein the particles comprise ZnO.

18. The method of claim 14 wherein the particles have a diameter distribution such that at least about 95 percent of the particles have a diameter greater than about 40 percent of the average diameter and less than about 160 percent of the average diameter.

19. The method of claim 14 wherein the particles have a diameter distribution such that at least about 95 percent of the particles have a diameter greater than about 60 percent of the average diameter and less than about 140 percent of the average diameter.

* * * * *